US00PP28046P3

(12) United States Plant Patent
Thompson

(10) Patent No.: US PP28,046 P3
(45) Date of Patent: May 23, 2017

(54) RASPBERRY PLANT NAMED 'PACIFIC STARLET'

(50) Latin Name: ***Rubus idaeus* L.**
Varietal Denomination: Pacific Starlet

(71) Applicant: Pacific Berry Breeding, LLC, Salinas, CA (US)

(72) Inventor: Ellen Thompson, Watsonville, CA (US)

(73) Assignee: Pacific Berry Breeding, LLC, Salinas, CA (US)

( * ) Notice: Subject to any disclaimer, the term of this patent is extended or adjusted under 35 U.S.C. 154(b) by 9 days.

(21) Appl. No.: 14/544,826

(22) Filed: Feb. 24, 2015

(65) Prior Publication Data

US 2016/0249508 P1 Aug. 25, 2016

(51) Int. Cl.
*A01H 5/08* (2006.01)

(52) U.S. Cl.
USPC ..... Plt./204

(58) Field of Classification Search
USPC ..... Plt./156, 203, 204
See application file for complete search history.

(56) References Cited

U.S. PATENT DOCUMENTS

| | | | |
|---|---|---|---|
| PP9,340 | P | 10/1995 | Wilhelm et al. |
| PP14,804 | P2 | 5/2004 | Fear et al. |
| PP17,819 | P3 | 6/2007 | Jennings |
| PP21,074 | P2 | 6/2010 | Aguas et al. |
| PP24,198 | P2 | 1/2014 | Finn |

OTHER PUBLICATIONS

U.S. Appl. No. 13/694,890, filed Jan. 16, 2013, Vinson.

*Primary Examiner* — Susan McCormick Ewoldt
*Assistant Examiner* — Karen Redden
(74) *Attorney, Agent, or Firm* — King IP Law; Joshua King

(57) ABSTRACT

A new and distinct cultivar of Raspberry plant named 'Pacific Starlet' as described and shown herein. 'Pacific Starlet' provides very firm berries which detach easily from the receptacle and maintain bright non-darkening color in postharvest cold storage.

5 Drawing Sheets

Latin name of the genus and species of the plant claimed: *Rubus idaeus* L.

Variety denomination: 'PACIFIC STARLET'.

BACKGROUND AND SUMMARY

The new raspberry cultivar designated 'Pacific Starlet' is shown herein. Botanically known as *Rubus idaeus* L., 'Pacific Starlet' is a primocane-fruiting raspberry that was discovered in a seedling field in May 2010 in Watsonville, Calif. 'Pacific Starlet' originated from open pollinated (OP) seed of an unknown variety. An increasing number of patented primocane-fruiting raspberries are discovered using material sourced from OP fruit. One example is the raspberry cultivar 'Vintage' (U.S. Plant Pat. No. 24,198), which was derived from open pollinated seed of the patented proprietary variety 'Isabel' (U.S. Plant Pat. No. 9,340). Another example is the variety 'Diamond Jubilee' (U.S. Plant Pat. No. 25,455), which was derived from open-pollinated fruit that was purchased in a retail store and thought to be the patented proprietary variety 'Driscoll Maravilla' (U.S. Plant Pat. No. 14,804).

The present cultivar, 'Pacific Starlet', offers significant advantages over the existing, patented primocane-raspberry cultivar 'Vintage' (U.S. Plant Pat. No. 24,198). For example, 'Pacific Starlet' offers typically firmer fruit than 'Vintage'. Another example of an existing patented primocane-raspberry is 'Marcela' (U.S. Plant Pat. No. 17,819). In contrast to 'Marcela', 'Pacific Starlet' has much larger fruit, though both are firm and have bright non-darkening color. A third example of an existing, patented primocane-raspberry variety is 'Pacific Deluxe' (U.S. Plant Pat. No. 21,074), a previous release from the same breeding program as the present cultivar, 'Pacific Starlet'. The present cultivar, 'Pacific Starlet' is a significant improvement over 'Pacific Deluxe' particularly for color; 'Pacific Deluxe' tends to darken significantly in postharvest cold storage, whereas 'Pacific Starlet' does not darken when picked and cold stored. Other improvements of 'Pacific Starlet' over 'Pacific Deluxe' include reduced fruit defects, easier fruit detachment, and lower acidity.

Thus, 'Pacific Starlet' is a new and distinct primocane-fruiting raspberry cultivar that can be identified, among other things, by its bright non-darkening berry color in cold storage, large size, ease of detachment and lower acidity. Further, leaf hue on the lower section of canes of 'Pacific Starlet' is distinct, with an upper color of The Royal Horticultural Society Colour Chart—Fifth Edition ("R.H.S.") 137D often flecked with the yellowish-green color RHS 151D.

BRIEF DESCRIPTION OF THE PHOTOGRAPHS

DETAILED DESCRIPTION

Figure 1:
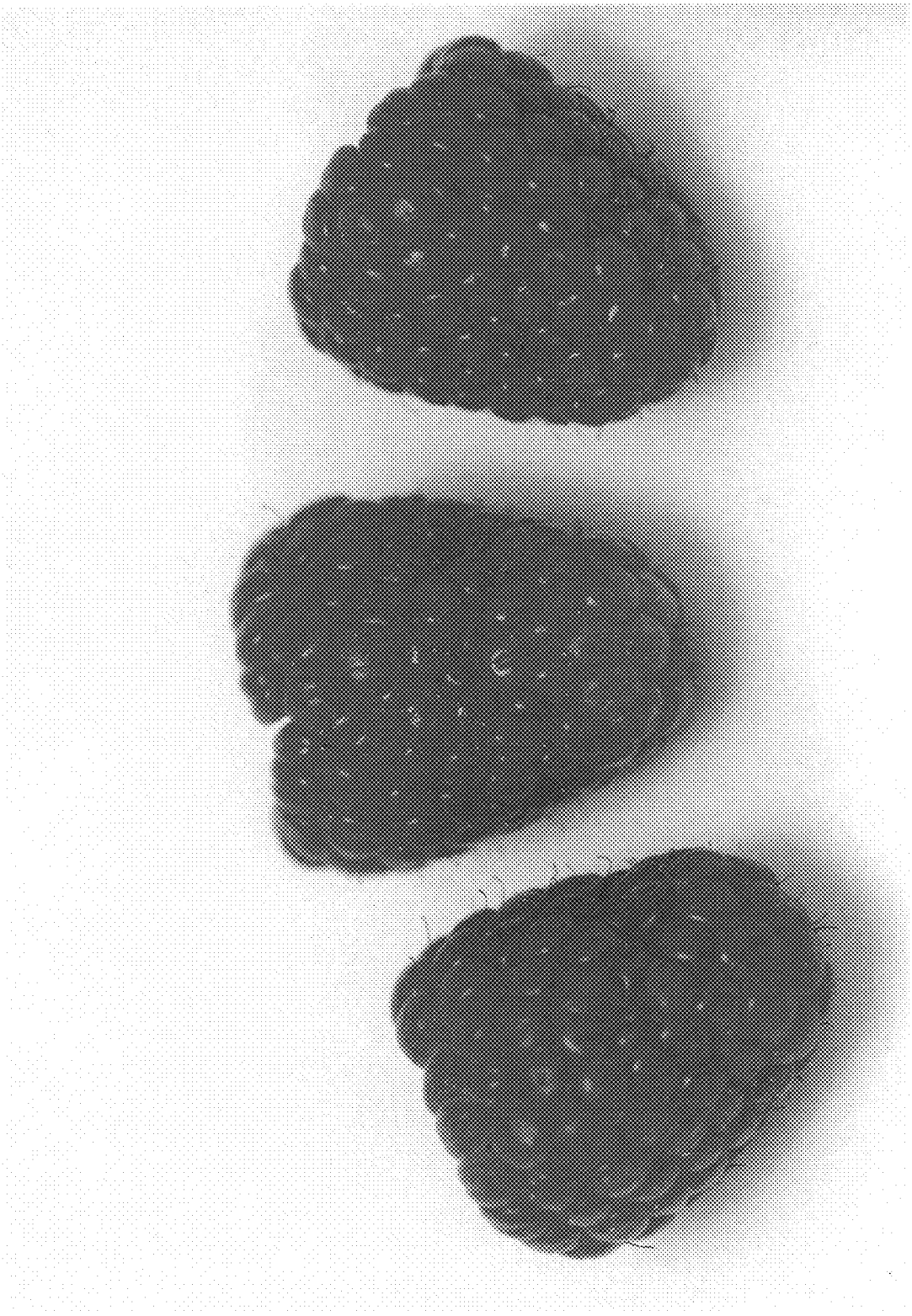
FIG. 1 is a close-up photograph showing the non-darkening, pink-red fruit color of the raspberry cultivar 'Pacific Starlet' to have an external fruit color of RHS 44A.
Figure 2:
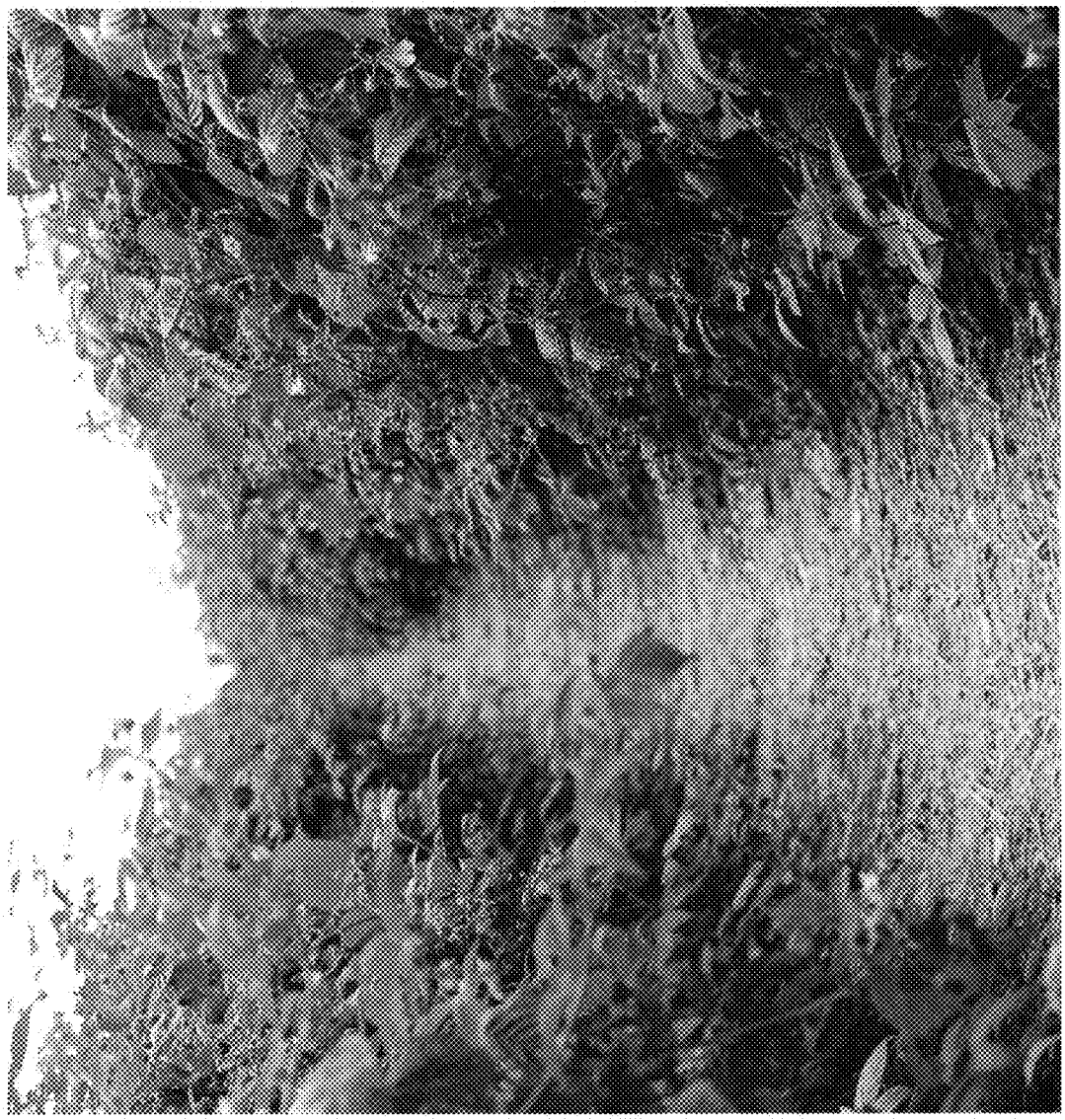
FIG. 2 is a photograph showing the canopy of the raspberry cultivar 'Pacific Starlet' having a crown age of about 3.5 years and a cane age of about 8 months.
Figure 3:
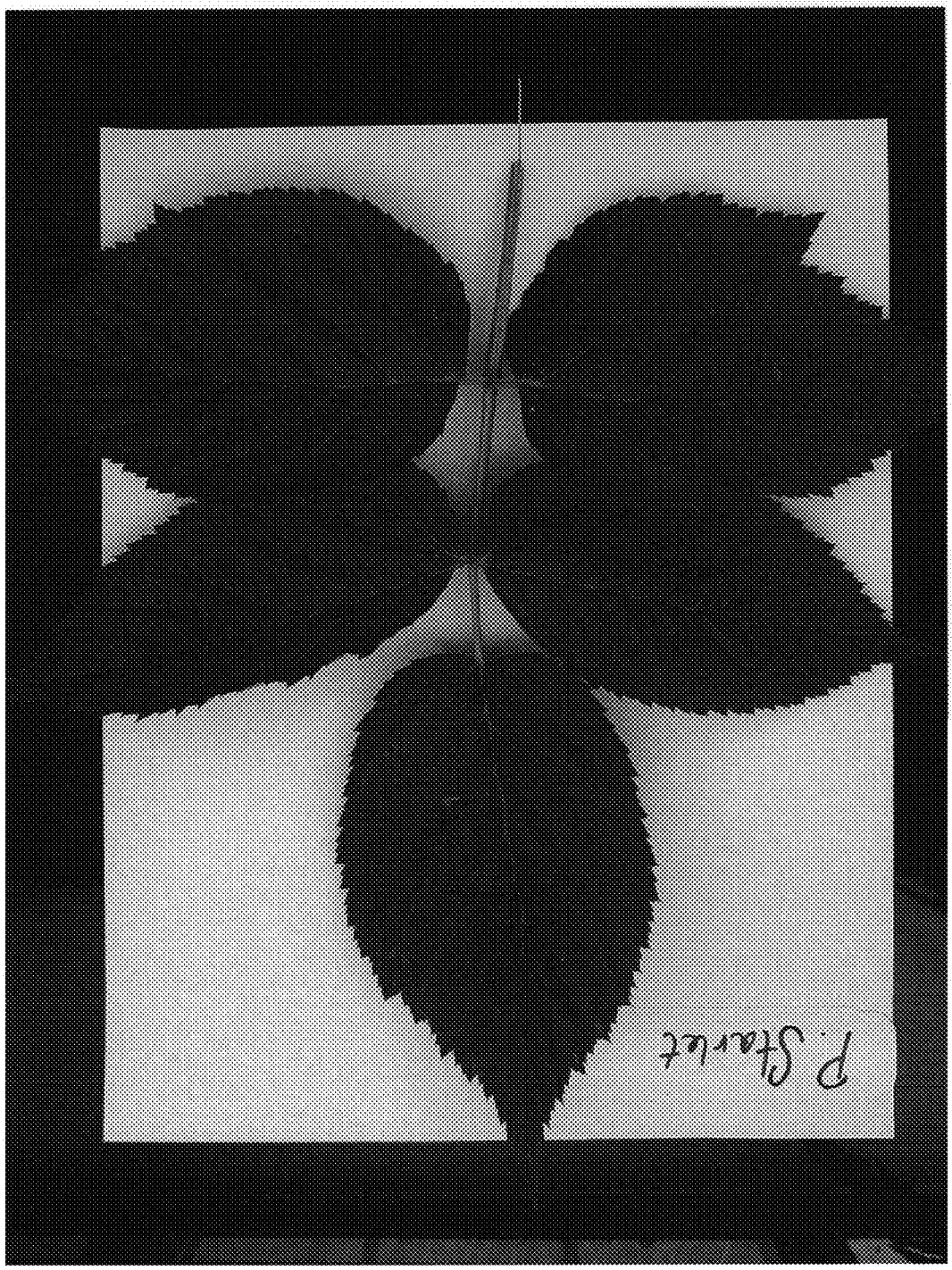
FIG. 3 is a close-up photograph of the distinctly pentafoliate leaves in the raspberry cultivar 'Pacific Starlet'. Note sessile attachment at the lateral leaf bases.
Figure 4:
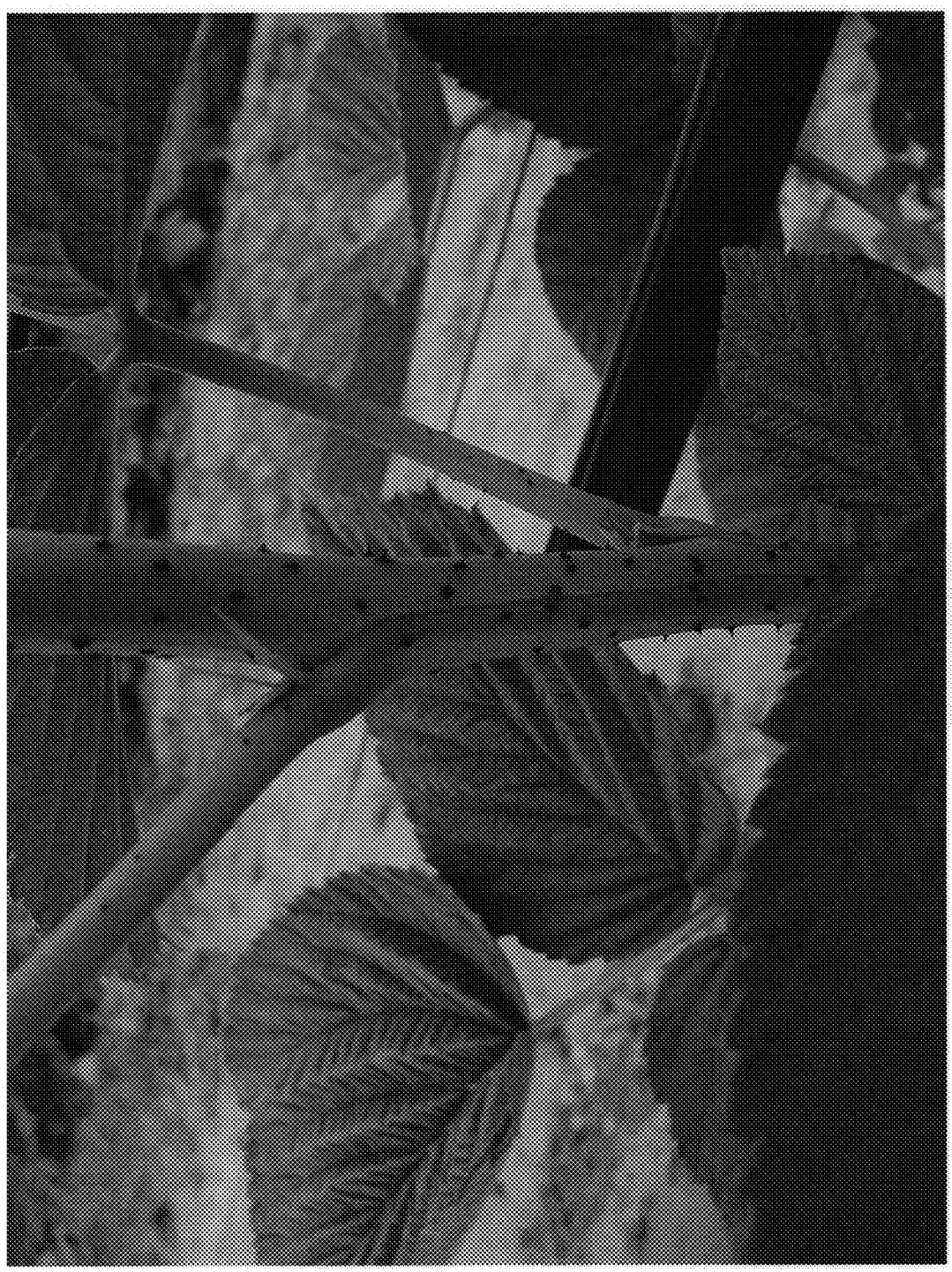
FIG. 4 is a detailed image of the darkly pigmented spines that are characteristic of the raspberry cultivar 'Pacific Starlet'.
Figure 5:
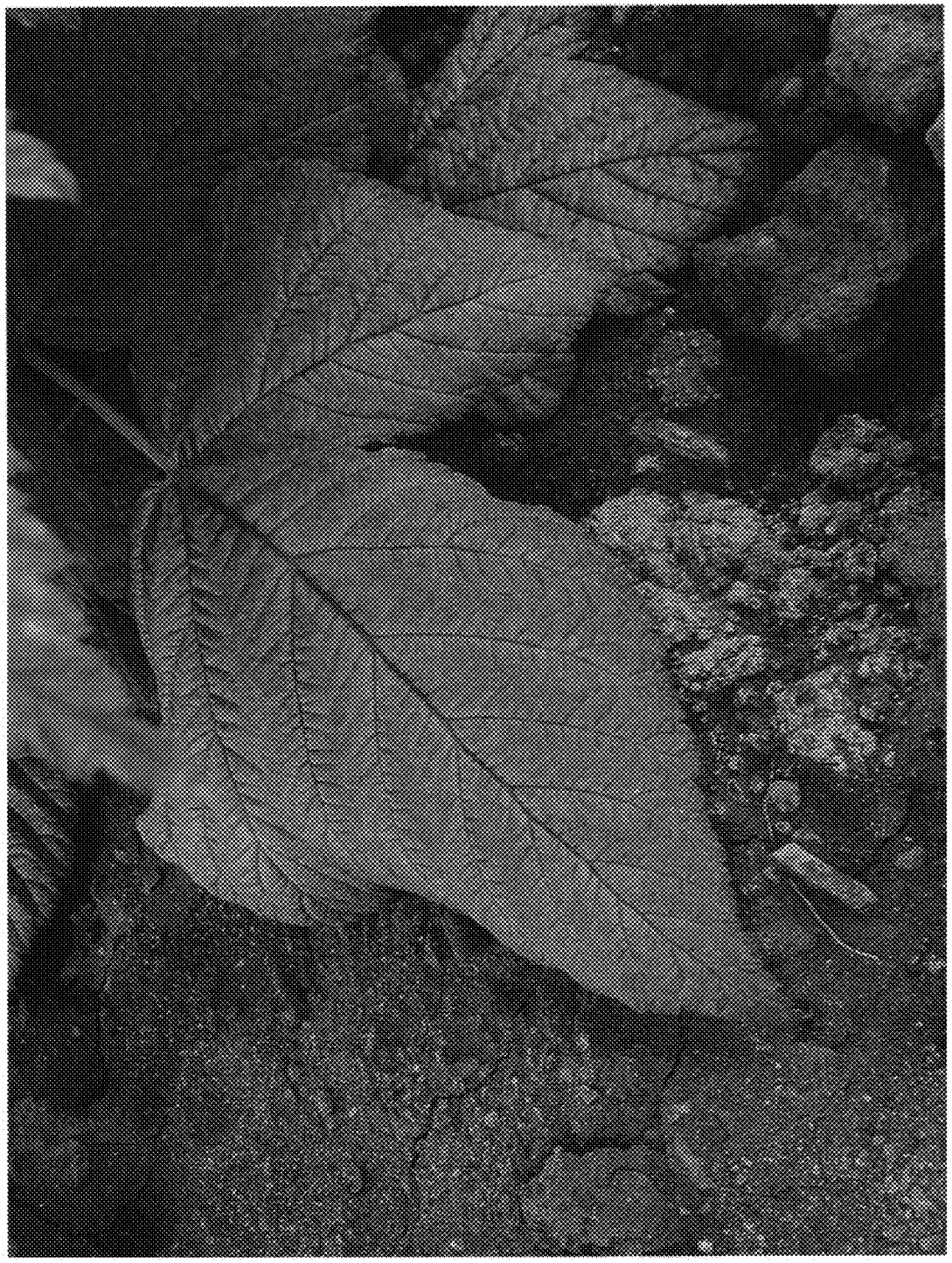
FIG. 5 is a photograph of the distinctly characteristic lower leaf coloration of the raspberry cultivar 'Pacific Starlet'. Lower leaves develop a mottled-chlorotic coloration during aging and senescence.

Note: Statements of characteristics herein represent exemplary observations of the cultivar herein and will vary depending on time of year, location, annual weather, etc.

Cultivar name: 'Pacific Starlet'.

Classification:

*Family*.—Rosaceae.

*Botanical name*.—*Rubus idaeus* L.

*Common name*.—Raspberry.

Parentage:

*Female parent*.—Unknown.

*Male parent*.—Unknown.

'Pacific Starlet' was first identified in a field with other seedlings in May 2010 at Watsonville, Calif. USA. 'Pacific Starlet' was first propagated asexually by crown division in August 2010 in Watsonville, Calif. USA. The crown on the original plant was dug and parted into basal cane pieces (approximately 15 cm long) with root attached and replanted into a selection plot elsewhere on the farm, resulting in a 3-fold increase.

In September 2011, two actively growing primocanes were dug (with root attached) and shipped to Lafayette, Oreg. USA, where vegetative material was explanted and established in vitro for micropropagation. This propagation method has allowed extensive testing of 'Pacific Starlet' and aided in determining that this cultivar is genetically stable.

Growing location for the observations herein: Watsonville, Calif. USA.

Time of year (season): Summer.

Age of plants used for this discussion: Crown age of about 3.5 years and a cane age of about 8 and 16 months for primocanes and floricanes, respectively.

Age of plants used for the photographs in the figures: Crown age of about 3.5 years and a cane age of about 8 and 16 months for primocanes and floricanes, respectively.

Type of greenhouse covering or growing structure, or field: High tunnel over a field planting.

Light: Natural.

Color terminology refers to The Colour Chart of The Royal Horticultural Society, Fifth Edition, London, United Kingdom (2007) ("R.H.S.").

Observations for floricanes herein were made in June 2013. Observations for primocanes herein were made in August 2013.

Plant:

*Form/shape*.—Vase.

*Growth habit*.—Erect.

*Height*.—1.9 m as measured from cane base to cane apex.

*Spread*.—40.8 cm as measured from lateral leaf tip to lateral leaf tip.

*Propagation method*.—Division.

*Time to initiate and develop roots*.—24 days.

*Root description*.—Generally of thick diameter with a smooth, glossy texture. Few feeder roots present. 'Pacific Starlet' generally produces spawn (shoots) from roots with moderate vigor.

Primocanes:

*Diameter*.—Base: 1.1 cm | Middle: 0.9 cm | Tip: 0.3 cm.

*Length*.—1.5-1.9 m.

*Number of nodes*.—37-42.

*Internode length*.—Base: 3.4 cm | Middle: 6.5 cm | Tip: 4.0 cm.

*Number of canes/hill*.—4-6.

*Cane color*.—RHS 144C.

*Spines* (*present or absent*).—Present. Density: Base: 28/cm$^2$ | Middle: 0.5/cm$^2$ | Tip: 2/cm$^2$. Shape: Acute. Length: 0.05 cm. Width: 0.01 cm. Apex descriptor: Lanceolate. Color: RHS 181A.

*Vegetative bud shape*.—Rounded. Length: 0.3 cm. Diameter (base): 0.2 cm. Diameter (tip): 0.08 cm. Color: RHS N200B. Texture: Mildly pubescent.

*Reproductive bud shape* (*base/tip*).—Truncate/acuminate. Length: 1.3 cm. Diameter (base): 0.98 cm. Diameter (tip): 0.12 cm. Color: RHS 146C. Texture: Pubescent.

Floricanes:

*Diameter*.—Base: 1.1 cm | Middle: 0.9 cm | Tip: 0.8 cm.

*Length*.—1.9 m.

*Number of nodes*.—14.

*Internode length*.—Base: 7.2 cm | Middle: 9 cm | Tip: 10.8 cm.

*Cane color*.—RHS 175A.

*Spines*.—Present. Spine density: Base: 28/cm$^2$ | Middle: 0.5/cm$^2$ | Tip: 2/cm$^2$. Spine shape: Acute. Spine length: 0.05 cm. Spine width: 0.01 cm. Spine apex descriptor: Lanceolate. Spine color: RHS 181A.

*Vegetative bud shape*.—Rounded. Length: 0.3 cm. Diameter (base): 0.2 cm. Diameter (tip): 0.08 cm. Color: RHS N200B. Texture: Mildly pubescent.

*Reproductive bud shape* (*base/tip*).—Truncate/acuminate. Length: 1.3 cm. Diameter (base): 0.98 cm. Diameter (tip): 0.07 cm. Color: RHS 146C. Texture: Pubescent.

*Winter hardiness*.—Unknown for 'Pacific Starlet' outside of USDA Hardiness Zone 9b (Watsonville, Calif.). This cultivar is best adapted to the mild coastal conditions of California.

*Drought/heat tolerance*.—Pollen viability and fruit quality of raspberry generally begins to decline above 30° C. This is consistent with observations of 'Pacific Starlet'. Raspberries are generally not drought tolerant, and 'Pacific Starlet' has not been tested in unirrigated plots.

Leaves:

*Complete leaf*.—Length: 19.8 cm. Width: 17.4 cm. Number of leaflets: 5.

*Terminal leaflet*.—Size: Length: 9.6 cm. Width: 7.2 cm. Length/Width ratio: 1.33. Shape of leaf apex: Acuminate. Shape of leaf base: Terminal leaf: Cordate. Shape of leaf base: Basal lateral leaflets: Sessile. Margin: Serrate. Texture: Mild interveinal puckering. Number of serrations/leaf: 96. Shape of serrations: Flexuous—Concave. Color: Upper Surface:

RHS 137A. Lower Surface: RHS 188C. Venation pattern: Reticulate. Venation Color: Upper surface: RHS N144D. Lower surface: RHS 145B. Leaf pubescence density: None, glabrous. Color of leaf pubescence: N/A. Number of leaflets/leaf: 3 on upper fruiting laterals. 5 on mid- to lower leaves. Interveinal blistering: Mild. Glossiness: Low.

*Primocane leaves*.—Petiole length: 4.1 cm. Petiole diameter: 2.0 cm. Petiole Color: Upper: RHS 137D. Lower: RHS 143D. Rachis length: 2.0 cm. Stipule length: 0.6 cm. Stipules per leaf: 2. Stipule Width: 0.01 cm. Stipule Color: RHS N144D. Color: Upper Surface: RHS 137A. Lower Surface: RHS 188C. Terminal leaflet: Length: 9.6 cm. Width: 7.2 cm. Rachis length: 0.8 cm. Basal lateral leaflet: Length: 7.2 cm. Width: 4.3 cm. Petiolule length: 0.1 cm.

*Floricane leaves*.—Petiole length: 4.8 cm. Stipule length: 0.4 cm. Stipules per leaf: 2. Stipule Width: 0.01 cm. Stipule Color: RHS N144D. Color: Upper surface: RHS 137A. Lower surface: RHS 188C.

*Terminal leaflet*.—Length: 9.0 cm. Width: 6.0 cm. Rachis length: 1.7 cm. Distal lateral leaflet: Length: 8.4 cm. Width: 6.0 cm. Petiolule: Length: 1.7 cm. Diameter: 0.1 cm. Color: Upper surface: RHS 137D. Lower surface: RHS 143D.

*Basal lateral leaflet*.—Length: 7.2 cm. Width: 4.2 cm. Petiolule Length: 0.1 cm. Diameter: 0.1 cm. Color: Upper surface: RHS 137D. Lower surface: RHS 143D.

Flowers:

*Time of flowering* (50% *of plants at first flower*).—August 5 on primocanes; April 15 on floricanes.

*Size*.—Length: 0.9 cm. Diameter: 0.7 cm.

*Fragrance*.—None.

*Peduncle*.—Length: 0.8 cm. Diameter: 0.05 cm. Color: RHS 143B. Pubescence: Present. Texture: Smooth with few undulations.

*Perianth*.—Flowering trusses shape: Truncate.

*Petals*.—Color (upper and lower): RHS 149D. Number per flower: 5. Shape: Oblanceolate. Length: 0.6 cm. Width: 0.1 cm. Apex descriptor: Rounded. Base Descriptor: Truncate. Margin descriptor: Entire. Texture: Smooth with visible striations.

*Sepals*.—Quantity: 5. Length: 0.6 cm. Width: Base — 0.3 cm. Mid — 0.1 cm. Tip — 0.01 cm. Color: RHS 145B. Apex descriptor: Acuminate. Margin descriptor: Entire. Texture: Mildly pubescent.

*Pedicel*.—Color: RHS 145A. Length: 0.9 cm. Diameter: 0.01 cm.

Reproductive organs:

*Self-fertile*.—Yes.

*Male*.—Stamen number: 90. Filament length: 0.3 cm. Filament diameter: 0.01 cm. Filament color: RHS 155C. Anther length: 0.01 cm. Anther diameter: 0.01 cm. Anther color: RHS 161C. Pollen Color: RHS 161C. Amount: Sparse.

*Female*.—Style length: 0.2 cm. Style diameter: 0.01 cm. Style color: RHS 154D. Stigma length: 0.2 cm. Stigma diameter: 0.01 cm. Stigma color: RHS 154D. Ovary color: RHS 145C. Ovary length: 1.2 mm. Ovary diameter: 0.45 mm.

Fruit:

*Predominant shape*.—Broad conic.

*Fruit weight*.—4.2 g.

*Fruit length*.—2.1 cm.

*Fruit width*.—1.75 cm.

*Fruit length/width ratio*.—1.2.

*Receptacle length*.—1.8 cm.

*Receptacle diameter*.—Base: 0.7 cm | Middle: 0.65 cm | Tip: 0.2 cm.

*Receptacle color*.—RHS 143B.

*Drupelet length*.—0.6 cm.

*Drupelet diameter*.—0.4 cm.

*Drupelet number*.—80.

*Drupelet weight*.—0.3 g.

*Fruit color external*.—RHS 44A.

*Fruit color internal*.—RHS 46A.

*Firmness of fruit skin*.—Very firm.

*Firmness of fruit flesh*.—Very firm.

*Hollow center*.—Present.

*Number of fruit per node*.—4-6.

*Time of ripening* (50% *of plants with first fruit*).—September 10 on primocanes.

*Time of fruiting*.—Early summer and autumn.

*Type of bearing*.—Remontant.

*Fruit yield*.—15,750 lb/a/cycle.

*Average brix°*.—8.2.

*Market use*.—Fresh.

*Keeping quality*.—Excellent.

*Shipping quality*.—Excellent.

Pest and disease resistance: 'Pacific Starlet' exhibits field tolerance to Raspberry Bushy Dwarf Virus (RBDV). Susceptibility to yellow rust (*Phragmidium rubi-idaei*) has been observed. This cultivar exhibits moderate field tolerance to *Phytopthora* root rot.

What is claimed is:

1. A new and distinct cultivar of Raspberry plant named 'Pacific Starlet' as described and shown herein.

* * * * *